(12) United States Patent
Deagle

(10) Patent No.: US 10,363,223 B1
(45) Date of Patent: Jul. 30, 2019

(54) DELAYED-RELEASE ENCAPSULATION OF DEER VELVET POWDER TO PROTECT THE DEER VELVET POWDER UNTIL MICELLIZATION AND ABSORPTION WITHIN THE TERMINAL ILLIUM

(71) Applicant: William R. Deagle, Vista, CA (US)

(72) Inventor: William R. Deagle, Vista, CA (US)

( * ) Notice: Subject to any disclaimer, the term of this patent is extended or adjusted under 35 U.S.C. 154(b) by 0 days.

(21) Appl. No.: 16/011,576

(22) Filed: Jun. 18, 2018

(51) Int. Cl.
| | |
|---|---|
| A61K 9/48 | (2006.01) |
| A61K 9/52 | (2006.01) |
| A61K 35/36 | (2015.01) |
| A61K 35/32 | (2015.01) |
| A61K 9/00 | (2006.01) |

(52) U.S. Cl.
CPC .......... *A61K 9/4833* (2013.01); *A61K 9/0065* (2013.01); *A61K 9/4816* (2013.01); *A61K 35/32* (2013.01); *A61K 35/36* (2013.01)

(58) Field of Classification Search
None
See application file for complete search history.

(56) References Cited

U.S. PATENT DOCUMENTS

| 8,067,364 B2 * | 11/2011 | Coates | A61K 35/36 514/7.6 |
| 8,765,188 B2 * | 7/2014 | Wang | A61K 35/14 424/529 |

FOREIGN PATENT DOCUMENTS

| CN | 1994321 | * | 7/2007 |
| CN | 106539955 | * | 3/2017 |

OTHER PUBLICATIONS

Derwent abstract of CN 106539955, Derwent accession No. 2017-27303A (2017).*
Machine translation of CN 106539955 (Mar. 2017).*
Derwent abstract of CN 1994321, Derwent accession No. 2008-A49279 (2008).*
Machine translation of CN 1994321 (Jul. 2007).*
Sui, Z. et al., "Bioactive components of velvet antlers and their pharmacological properties," Journal of Pharmaceutical and BViomedical Analysis, vol. 87, pp. 229-240 (2014).*
Zhang, H. et al., "Toxicological evaluation of New Zealand deer velvet powder. Part I: acute and subchronic oral toxiciity studies in rats," Food and Chemical Technology, vol. 38, pp. 985-990 (2000).*
Elsevier—Journal homepage: www.elsevier.com/locate/lwt LWT—Food Science and Technology 60 (2015) pp. 544-551 Article available online Sep. 19, 2014 "A novel hypromellose capsule, with acid resistance properties, permits the targeted delivery of acid-sensitive products to the intestine".
Vivo Pathophysiology—http://www.vivo.colostate.edu/hbooks/pathphys/digestion/smallgut/absorb_lipids.html Article—downloaded Jun. 16, 2018 "Absorption of Lipids".
Nutraceutical Business Review—www.nutraceuticalbusinessreview.com Article dated May 15, 2014 "Capsugel DRcaps capsules selected by Quest for new probiotic line".
Hindawai Publishing Corporation—http://dx.doi.org/10.1155/2014/540580 vol. 2014, Article ID 540580, 10 pages, published Feb. 20, 2014 "Deer Antler Extract Improves Fatigue Effect through Altering the Expression of Genes Related to Muscle Strength in Skeletal Muscle of Mice".
Ulprospector—https://www.ulprospector.com/en/na/Food/Detail/6667/224847/DRcaps-Acid-Resistant-Hypromellose-Caosules Article downloaded Jun. 16, 2018 "DRcaps™ Acid Resistant Hypromellose Capsules".
Cell Press Molecular Cell, vol. 4, 299-308, Sep. 1999 Article—"Identification of the Major Intestinal Fatty Acid Transport Protein".
HHS Public Access—https://www.ncbi.nlm.nih.gov/pmc/articles/PMC3996833/ Article—published online Sep. 18, 2013 "New insights into the molecular mechanism of intestinal fatty acid absorption".
HHS Public Access Article—Published in final edited form Apr. 2016 "Physiology of Intestinal Absorption and Secretion".
Capsugel Library—www.capsugel.com Published study, 2012 "Protection of probiotics filled in non coated DRcapsTM acid resistant Hypromellose capsules".
PLOS ONE—www.plosone.org Article—Jan. 2012 | vol. 7 | Issue 1 | e30026 "Proteomes and Signalling Pathways of Antler Stem Cells".
GEN2OPLUS—http://genf2Oplus.info/the-benefits-of-deer-velvet-antler-and-the-history-behind-it.php Article—2018 "The Benefits of Deer Velvet Antler and the History Behind It".
Hindawai Publishing Corporation—http://dx.oi.org/10.1155/2015/819520 Article—vol. 2015, Article ID 8199520, 10 pages "The Effects of Elk Velvet Antler Dietary Supplementation on Physical Growth and Bone Development in Growing Rats".
Bioprotein Technology—www.bioproteintech.com Research manual—Velvet Antler research and findings.
naturessources.com—https://naturessources.com/products/mountain-red-deer-velvet Product information—2012 "Mountain Red Deer Velvet Natural Health Supplement".

(Continued)

*Primary Examiner* — John Pak
(74) *Attorney, Agent, or Firm* — Russ Weinzimmer & Associates, P.C.

(57) ABSTRACT

An encapsulation of deer velvet powder for ensuring delivery of the deer velvet powder to the terminal ileum of the small intestine, thereby ensuring micellization of unaltered molecules of the deer velvet powder, and systemic delivery of the unaltered molecules to all the organs of the body for regeneration and repair. The encapsulation includes: a delayed release capsule, and deer velvet powder contained within the delayed release capsule. The delayed release capsule is acid resistant, thereby protecting the deer velvet powder from digestive processes while transiting the stomach and upper small intestine, enabling the deer velvet powder to be released substantially along the terminal ilium of the small intestine so as to ensure micellization and absorption of unaltered molecules of deer velvet. Thus, swallowing the deer velvet powder encapsulated in a delayed release capsule delivers more of the benefits of deer velvet than standard encapsulations of deer velvet.

14 Claims, 2 Drawing Sheets

(56) References Cited

OTHER PUBLICATIONS

Capsugel—capsugel.com/drcaps Study results—2014 "DRcaps® Capsules Achieve Delayed Release Properties for Nutritional Ingredients in Human Clinical Study" "A gamma-scintigraphy study confirms delayed release properties of DRcaps capsules in human subjects".

Elk Tech International Article by Dr. John S. Church "Velvet Antler—It's historical medical use, performance enhancing effects and pharmacology".

Capsugel—www.capsugel.com Informational material—2011 "DRcaps acid resistant hypromellose capsules" "Balance between protection and targeted release".

* cited by examiner

DELAYED-RELEASE ENCAPSULATION OF DEER VELVET POWDER TO PROTECT THE DEER VELVET POWDER UNTIL MICELLIZATION AND ABSORPTION WITHIN THE TERMINAL ILLIUM

FIELD OF THE INVENTION

This invention relates to encapsulated nutritional supplements, and more particularly to encapsulated deer velvet powder.

BACKGROUND OF THE INVENTION

Deer velvet is the tissue that covers the bone and cartilage that develop into deer antlers. Also called "Deer antler velvet", "antler velvet", "velvet antler", and "red deer velvet", it has been harvested for centuries, and has been used traditionally to increase strength, boost the immune system, and counter the effects of stress, as well as being used as a remedy for a wide range of health problems.

An example of a high quality deer velvet encapsulated product is Mountain Red™ Deer Velvet, made and sold by Mountain Red™ Limited, Richmond, Nelson, New Zealand. Mountain Red™ Deer Velvet is encapsulated in 00 size gelatin capsules, and contains IGF-1 & IGF-2, which are a class of polypeptides similar to those found in steroids. There are also over 396 active ingredients naturally present in deer velvet that include a variety of proteins, amino acids, phospholipids, collagen, lipids, minerals, trace elements, growth factors, growth hormones, prostaglandins, glucosamine, chondroitin, and glycosaminoglycans. 00 size gelatin capsules release their contents into the stomach about five minutes after swallowing.

There is potential for deer velvet to aid in tissue regeneration (based on some in vitro studies), and the idea of somehow acquiring the massive regenerative properties of deer antlers is encouraging. However, the idea of consuming deer velvet in standard gelatin capsules for enabling tissue regeneration is not presently supported by competent scientific studies.

Moreover, the regeneration-enhancing properties of deer velvet powder appear to be related to bioactive polypeptides. However, it is likely that a substantial percentage of the bioactive polypeptides, along with other complex biomolecules components of deer velvet, are digested by stomach acid and reduced to more simple molecules before being absorbed, which would make oral consumption of deer velvet powder substantially reduced in health benefits.

For example, two studies examining the effects of deer velvet supplements taken by athletes have yielded conflicting results. One study showed some improvements in endurance and knee strength in weightlifters, but the other study found no improvements in rowers after 10 weeks of supplementation with deer velvet.

Consequently, delivering the benefits of an acid-sensitive supplement, such as deer velvet, can be a challenge. Protecting ingredients from stomach acid to maintain effectiveness is crucial—but it can require complex enteric coating formulations and manufacturing techniques, expensive packaging, and the use of solvents that many dietary supplement consumers find unacceptable.

More specifically, conventional film coatings for stomach acid-resistance involve costly manufacturing processes that lead to waste, delays, and yield loss. Further, cumbersome tablet-coating and microencapsulation techniques require use of chemicals that do not conform to many consumers' preference for 'healthy and natural' products. Additionally, heat used in the coating process can damage the delicate biomolecules before they are consumed.

SUMMARY OF THE INVENTION

In utero, the placenta provides to the fetus the building blocks for growth and regeneration, including eight molecular classes of about 300 biomolecules for structural proteins and enzymes, and at least six major hormones for regeneration. Although time passes for the fetus in utero, this is the only stage of life in which aging does not clinically occur.

Generally, stem cells play a crucial role in tissue and organ formation and in regeneration. Deer antler provides a single organ model in which growth and development are controlled by the proliferation and differentiation of tissue specific stem cells with embryonic-like properties As recognized by the invention, deer velvet has the same eight molecular classes of about 300 biomolecules for structural proteins and enzymes, and the same at least six major hormones for regeneration, as those that the placenta provides to the fetus in utero.

Even though oral consumption of deer velvet in conventional gelatin capsules destroys the molecular integrity of the deer velvet with stomach acid, pepsin, and pancreatic digestive enzymes, according to the invention, consuming deer velvet orally in a delayed-release acid-resistant capsule that is targeted to release the deer velvet in the lower small intestine, PROTECTS the molecular integrity of the deer velvet from stomach acid, pepsin, and pancreatic digestive enzymes. Since the delayed-release acid-resistant capsule PROTECTS the molecular integrity of the deer velvet while passing through the stomach and the upper small intestine, the full nutritional and health benefits of the deer velvet powder can be delivered to the lower small intestine so that it can be micellized and absorbed in the terminal ilium at the end of the small intestine.

The deer velvet powder released by a delayed-release acid-resistant hypromellose capsule into the lower small intestine, is then transformed by the terminal ilium of the small intestine into micelles containing "building blocks" for enabling the stem cells to facilitate somatic regeneration. The terminal ileum performs the micellar transformation of biomolecules found in deer velvet, thereby making the biomolecules available to stem cells throughout the body.

The eight classes of biomolecules numbering about three hundred, and the six primary growth hormones, are transported exclusively across the terminal ileum after micellization. These molecules are protected by the acid-resistant delayed release capsules while passing through the stomach and upper small intestine, and thus are not altered by the stomach acid, pepsin, and digestive enzymes from the pancreas. The stem cells requires these molecules for all organ regeneration. The stem cells act as architects or engineers, marshalling the molecules and hormones to regenerate the body, analogous to processes occurring in the placenta during the fetal state, where the placenta generates the same molecular classes and growth hormones. Aging does not occur in utero in a fetus, and deer velvet powder targeted for delivery to the lower small intestine by oral consumption of deer velvet powder encapsulated in a delayed release capsule according to the invention is meant to reproduce the conditions of zero aging in the fetal state.

DRcaps® brand delayed release acid-resistant capsules, sold by Capsugel®, a Lonza® company, can be used as the delayed release acid-resistant capsules that encapsulate the deer velvet powder for oral consumption, and protect the deer velvet powder from degradation while passing through the stomach and upper small intestine. DRcaps® delayed release capsules allow release of the deer velvet powder AFTER leaving the stomach, so that the deer velvet powder is released along the lower small intestine, ideally within the terminal ilium.

In fact, a scintigraphic in vivo study demonstrated that the release of the contents from DRcaps® occurs after the capsules have passed through the stomach. Thus, DRcaps® delayed release capsules protect the vulnerable components of deer velvet, such as polypeptides, from degradation by stomach acid, and other digestive secretions in the stomach.

DRcaps® delayed release capsules are made using hypromellose (HPMC) that helps to protect sensitive ingredients from the low pH (acidic) environment of the stomach—without the cost and complexity of adding acid-resistant properties during manufacturing.

Hypromellose, also called hydroxypropyl methylcellulose (HPMC), is a semisynthetic, inert, viscoelastic polymer. As a food additive, hypromellose is used as an alternative to animal gelatin.

Further, the low moisture level inside of a DRcaps® capsule can also be exploited to protect hygroscopic ingredients, such as can be found in deer velvet powder.

A study was performed to demonstrate DRcaps® delayed release capsules disintegration performance in human subjects. The study was designed to investigate the in vivo behavior of unbanded DRcaps® delayed release capsules using qualitative and quantitative scintigraphic methods to assess the GI transit of DRcaps® delayed release capsules, and the release of capsule contents based on the scintigraphic images thereby obtained. Each subject consumed a light breakfast approximately 30 minutes prior to consuming a DRcaps® delayed release capsule containing 300 mg of lactose, 10 mg of which was radio-labelled with a radioisotope. Anterior and posterior images were taken after dosing, and then every 5 minutes up to four hours after consumption of the capsule.

The study showed that DRcaps® delayed release capsules displayed delayed release properties, where disintegration of the capsule started approximately 45 minutes later than a typical immediate release capsule (e.g., a gelatin capsule), which disintegrated after about 5 minutes. For the majority of subjects, complete release took place in the small intestine, not in the stomach. Complete release of contents from the DRcaps® delayed release capsules occurred 20 minutes after the onset of release. Thus, DRcaps® delayed release capsules significantly reduced the possibility of ingredient degradation in the stomach as compared with a standard immediate release capsule, such as a gelatin capsule.

Use of delayed release acid-resistant capsules avoid the need for complex enteric coating formulations and manufacturing techniques, expensive packaging, and use of solvents that many dietary supplement consumers find unacceptable. Delayed release capsules also do not require the use of chemicals, additives, or excipients, which is consistent with many consumers' preference for 'healthy and natural' products. Since heat is not used in the encapsulation process, the delicate biomolecules of the deer velvet can be delivered to the terminal ilium in their pristine state.

When any capsule is swallowed, it must pass through the gastrointestinal tract to be absorbed. The human gastrointestinal tract is divided into the upper gastrointestinal tract and the lower intestinal tract.

The upper gastrointestinal tract includes the stomach, and the duodenum of the small intestine. The small intestine is the part of the gastrointestinal tract between the stomach and the large intestine. The small intestine is where most of the absorption of food takes place.

The lower gastrointestinal tract includes the rest of the small intestine, and all of the large intestine.

In humans, the small intestine is subdivided into the duodenum, the jejunum, and the ileum. The duodenum can also be called the "upper small intestine".

The duodenum is a short structure ranging from 0.20 m (7.9 inches) to 0.25 m (9.8 inches) in length. It receives gastric chyme from the stomach, together with digestive enzymes from the pancreas, and bile from the liver. The digestive enzymes break down proteins, and bile emulsifies fats into micelles.

The jejunum is the midsection of the small intestine, connecting the duodenum to the ileum, and is about 2.5 m long.

The ileum is the final section of the small intestine, and is about 3 m long. It absorbs mainly vitamin B12 and bile acids, as well as any other remaining nutrients. The ileum joins to the cecum of the large intestine at the ileocecal junction, where the terminal ileum communicates with the cecum of the large intestine through the ileocecal valve. The pH along the ileum is usually between 7 and 8 (neutral to slightly alkaline). The ileum has an extremely large surface area both for the adsorption (attachment) of enzyme molecules, and for the absorption of products of digestion. The villi of the ileum contain large numbers of capillaries that take the amino acids and glucose produced by digestion to the hepatic portal vein to the liver. Lacteals are small lymph vessels, and are present in villi. Lacteals absorb fatty acid and glycerol, the products of fat digestion.

According to the invention, pure pristine deer velvet powder encapsulated in delayed release capsules can deliver to the terminal ilium of the small intestine a pristine (undigested and otherwise unmodified during transit through the gastrointestinal tract) molecular array of "building blocks" for enabling the stem cells of the body to facilitate somatic regeneration, which "building blocks" are then sent via the terminal ilium to the general circulation for rebuilding any organ of the body. Thus, pure pristine deer velvet powder encapsulated in delayed release capsules according to the invention facilitates organ regeneration by supporting the stem cells, the architects of body organ regeneration. Accordingly, there is reason to believe that the invention can be used halt or possibly even reverse aging and loss of organ function, as we age and/or if we become injured.

For example, in the teen years of humans, the body produces relatively good levels of IGF-1. The production of IGF-1 in turn leads to the production of growth hormones, which is why most teens have low body fat and lean muscle mass. However, as one ages, the body produces less IGF-1, which means less production of HGH. As a result, the signs of aging begin to appear, including wrinkles, fatigue, abdominal fat, loss of lean muscle, and a decrease in libido.

"IGF-1" or Insulin-like Growth Factor-1," is a natural hormone factor. High levels of Insulin-like Growth Factor-1 have been found in deer blood during the period where their antlers are growing. Also, it is well established that IGF-1 is a component of deer velvet. According to the invention, IGF-1 of the deer velvet is transported via the terminal ilium for use by the rest of the body.

As the only known example of complete organ regeneration in mammals, deer antler in the growing or velvet phase is of major interest in developmental biology. This regeneration event initiates from self-renewing antler stem cells that exhibit pluripotency.

The molecular pathways and transcription factors identified in deer antler in the growing or velvet phase are common to embryonic and adult stem cells. However, expression of embryonic stem cell transcription factors suggests that antler stem cells are an intermediary stem cell type between embryonic and the more specialized tissue-specific stem cells like those residing in muscle, fat, or from a hematopoietic origin. The retention of this embryonic, pluripotent lineage may be of fundamental importance for the subsequent regenerative capacity of antlers.

The annual full regeneration of deer antlers is unique among mammals and the evidence to date indicates that it is a stem cell based process. Antler regeneration occurs in yearly cycles consisting of growth, calcification, antler skin (also known as velvet) shedding, and antler casting. During the growth phase, antlers are made up of cartilage and bone infiltrated with blood vessels and nerve networks, and are covered by a velvet skin. Generally, stem cells play a crucial role in tissue and organ formation, and in regeneration.

Deer antler provides a single organ model in which growth and development are controlled by the proliferation and differentiation of tissue specific stem cells with embryonic like properties. Antler stem cells are an invaluable model for investigating these fundamental biological phenomena. A recent study showed that the pool of stem cells from which antler regeneration initiates resides in the periosteum of a permanent bony extension from the deer skull termed the pedicle. Pedicles that are deprived of the enveloping periosteum do not regenerate antlers. Thus the cells are termed the pedicle periosteum cells (PP cells). The antler bud forms from the pedicle periosteum, and the velvet antler then grows from the cells of the mesenchyme located at the tip of the main beam and the tines once the antler branches form. The exact molecular mechanism by which velvet antler develops from the pedicle is not yet fully understood. Growth of the pedicle itself is initiated during puberty from a different pool of stem cells located in a zone named the antlerogenic periosteum (AP cells), which covers a crest in the deer skull located just above the eye socket. Removal of the AP prior to pedicle initiation stops pedicle and antler growth, while transplantation of the AP induces ectopic pedicle and antler formation.

Once the pedicles reach approximately 6 cm in height in red deer, the first antlers emerge from their apices. Subsequent antler growth cycles are under the control of androgen hormones, and are influenced by environmental conditions. In utero, a primordial pedicle begins to grow at about 60 days of gestation, and continues to develop until about 100 days when growth slows. By the time the calf is born the pedicles are not noticeable. There is evidence to suggest that the antlerogenic periosteum (AP) in the adult is a piece of retained embryonic tissue, which may, therefore, retain embryonic stem cell capabilities, i.e. pluripotency.

Deer velvet includes the "Building Blocks of Life" for delivery by micellization and absorption via the terminal ileum so as to provide support for stem cells systemically. These building blocks of life include: beneficial growth factors, saturated fatty acid molecules, phospholipids, minerals, glycosaminoglycans, extracellular matrix components, a complete array of amino acids.

Delayed release capsules protect these fragile eight classes of building block molecules, and scalar transmembrane stem cell regenerative signal transducer molecules, from degradation by acid and pepsin enzymes in the stomach, and from pancreatic digestive enzymes. Mycellization in the terminal ileum allows these active molecules, which are analogous to placenta building block molecules used by the fetus, to amplify and allow stem cell mediated organ and tissue regeneration and "fractional cloning" every night.

Every night in Stage 4 REM sleep, the pineal gland, hypothalamus, and pituitary gland send growth signals via human growth hormone (HGH), and many other hormones, as well as harmonic resonant DNA signaling via fascia connective tissue and myelinated and non-myelinated nerves, to target tissues and organs so as to direct epigenetic organ rejuvenation, i.e., fractional cloning of cells, organs, and tissues every night. This process is systematic, and when disrupted due to deficient sleep, lack of stem cell release, or deficiency of building block molecules and hormones, organ regeneration does not occur optimally. This results in accelerated aging. Thus, consuming deer velvet in a delayed release capsule according to the invention provides building block molecules and hormones, thereby facilitating fractional cloning of stem cells, organ regeneration, and trauma recovery.

A general aspect of the invention is an encapsulation of deer velvet powder for ensuring delivery of unaltered molecules of the deer velvet powder systemically to organs of a body for regeneration, the body having a stomach and a small intestine, the small intestine having a terminal ilium. The encapsulation includes: a delayed release capsule, the delayed release capsule configured to contain a quantity of deer velvet powder, the delayed release capsule configured to resist digestive processes in the stomach so as to release the deer velvet powder substantially along the small intestine, thereby ensuring micellization and absorption of various components of the deer velvet powder along the terminal ilium; and a quantity of deer velvet powder, the quantity of deer velvet powder being contained within the delayed release capsule.

In some embodiments, the delayed release capsule is of size 00.

In some embodiments, the quantity of deer velvet powder is substantially 500 mg.

In some embodiments, the delayed release capsule is configured to release the quantity of deer velvet powder about 50 minutes after swallowing the capsule containing the quantity of deer velvet.

In some embodiments, the delayed release capsule is made using hypromellose (HPMC).

In some embodiments, the delayed release capsule includes a gelling agent.

In some embodiments, the quantity of deer velvet powder is anesthetic-free.

In some embodiments, the quantity of deer velvet powder is obtained by carefully grinding the deer velvet powder off antlers of a deer without including antler bone.

In some embodiments, the quantity of deer velvet powder is obtained by maximized harvesting with peak molecular timing for collection coordinated with the date and season for best molecular and hormonal content.

In some embodiments, the quantity of deer velvet powder is obtained by using pneumatic bladder capture of animals in dark huts for careful antler recovery and gentle animal recovery without anesthetic.

Another general aspect of the invention is a method for manufacturing an encapsulation of deer velvet powder for ensuring delivery of unaltered molecules of the deer velvet powder systemically to organs of a body for regeneration, the body having a stomach and a small intestine, the small intestine having a terminal ilium. The method includes: obtaining a delayed release capsule, configured to contain a quantity of deer velvet powder; obtaining a quantity of deer velvet powder; and filling the delayed release capsule with the quantity of deer velvet powder.

In some embodiments, the delayed release capsule is of size 00.

In some embodiments, the quantity of deer velvet powder is substantially 500 mg.

In some embodiments, the delayed release capsule is configured to release the quantity of deer velvet powder substantially along the small intestine.

In some embodiments, the delayed release capsule is configured to release the quantity of deer velvet powder during transit through the small intestine about 50 minutes after swallowing the delayed release capsule and the quantity of deer velvet contained therein.

In some embodiments, the delayed release capsule is made using hypromellose (HPMC).

Yet another general aspect of the invention is a method for naturally promoting micellization of deer velvet powder so as to deliver unaltered molecules of the deer velvet powder systemically to organs of the body for regeneration, the body having a stomach and a small intestine. This method includes swallowing an encapsulation of deer velvet powder in a delayed release capsule.

In some embodiments, the delayed release capsule is acid resistant, so as to transit the stomach and enter the lower small intestine before releasing the deer velvet powder.

In some embodiments, the delayed release capsule is configured to release a substantial amount of the deer velvet powder within the terminal ilium.

In some embodiments, the delayed release capsule is made using hypromellose (HPMC) and a gelling agent.

BRIEF DESCRIPTION OF THE DRAWINGS

Many additional features and advantages will become apparent to those skilled in the art upon reading the following description, when considered in conjunction with the accompanying drawings, wherein.

DETAILED DESCRIPTION

Figure 1:
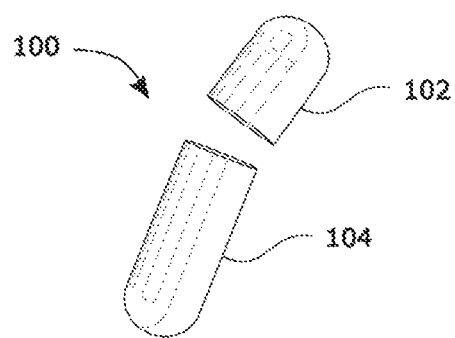
FIG. 1 is an isometric view showing a top half of an empty delayed release capsule, and a bottom half of an empty delayed release capsule.

With reference to FIG. 1, an empty delayed release capsule 100 is shown in a condition prior to filling. The empty delayed release capsule 100 includes a top half 102, and a bottom half 104.

Figure 2:
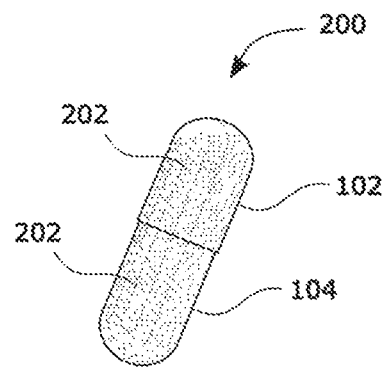
FIG. 2 is an isometric view showing the delayed release capsule of FIG. 1 filled with deer velvet powder in accordance with an embodiment of the invention.

With reference to FIG. 2, a filled delayed release capsule 200 is shown in a filled condition. The filled delayed release capsule 200 includes the top half 102 and the bottom half 104, joined together so as to securely contain a quantity of deer velvet powder 202 in accordance with an embodiment of the invention.

Figure 3:
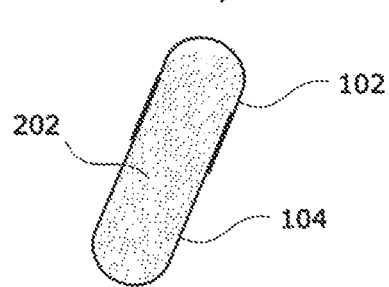
FIG. 3 is a cross-sectional view of the assembled and filled delayed release capsule of FIG. 2.

With reference to FIG. 3, a cross-sectional view is shown of the filled delayed release capsule 200 of FIG. 2.

Figure 4:
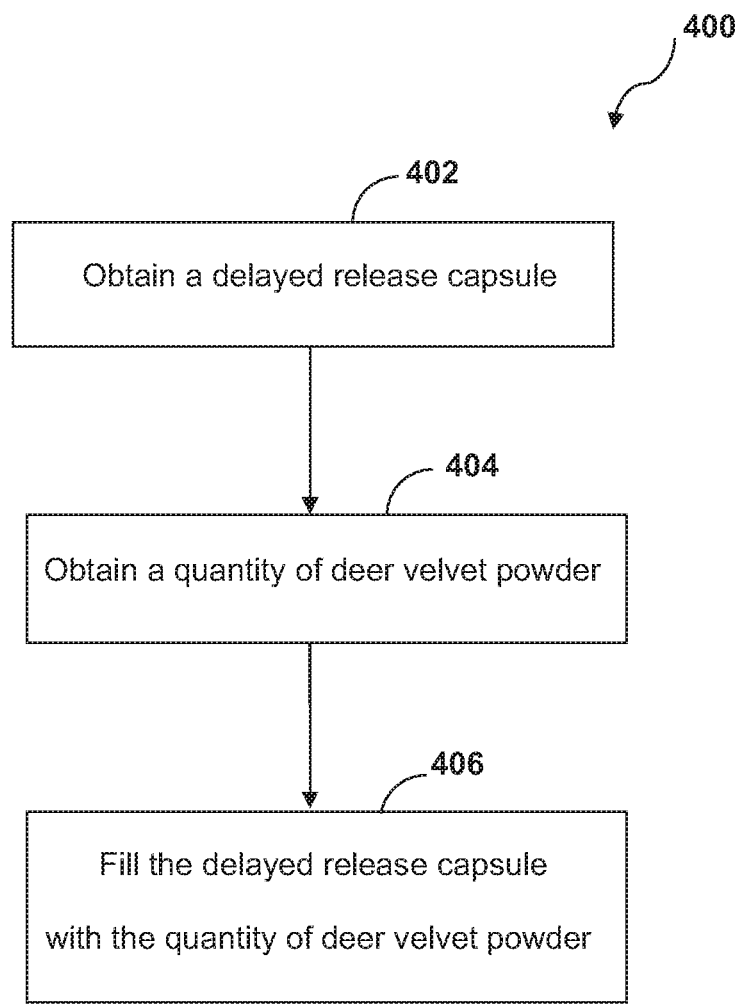
FIG. 4 is a flow diagram showing the steps of a method for manufacturing an encapsulation for ensuring delivery of deer velvet powder to the terminal ileum.

With reference to FIG. 4, a flow diagram is presented showing the steps of a method 400 for manufacturing an encapsulation for ensuring delivery of a quantity of deer velvet powder 202 to the terminal ileum according to the invention. The method 400 includes: obtaining 402 a delayed release capsule sized to contain a quantity of deer velvet powder; obtaining 404 a quantity of deer velvet powder; and filling 406 the delayed release capsule with the quantity of deer velvet powder.

To fill 406 the delayed release capsule 100 with the quantity of deer velvet powder 202, such as 500 mg of deer velvet powder, first take a 5 Kg batch of pure non-irradiated sterile deer velvet powder, and place it in a standard encapsulation machine. The standard encapsulation machine must be able to completely fill a plurality of about 10,000 "00" Size delayed release capsules with 500 mg of pure sterile deer velvet powder in each 00 capsule. No excipients, fillers, or flow agents are included—just pure non-irradiated sterile deer velvet powder. This will provide enough capsules to fill 166 bottles with 60 capsules each.

Only harvested BSE-Free, anesthetic free, gently harvested deer velvet that is sterile can be used. This level of quality deer velvet is best obtained from New Zealand, where several suppliers that meet these criteria currently operate.

A bottle of 60 capsules would be about a month's supply per bottle if taking two capsules per day, which would be a minimum recommended dose. Generally, one to two capsules should be taken two to three times per day. Thus, one bottle might last for ten days if taking six capsules per day, and therefore three bottles would be needed per month at the higher recommended dose to obtain the benefits of consuming the deer velvet encapsulation of the invention.

An embodiment of the delayed release capsule is the acid resistant DRcaps™ delayed release capsules, which are made using hypromellose (HPMC) so as to protect the deer velvet contained in the capsule from the low pH (acidic) environment of the stomach. Other ingredients of the DRcaps™ delayed release capsules include a gelling agent (Gellan gum) and water. DRcaps™ delayed release capsules will tolerate pH down to 2.0, and thereby resisit exposure to stomach acid, pepsin, and digestive enzymes. DRcaps™ delayed release capsules are more robust than standard capsules, e.g., gelatin capsules, when exposed to stomach acid, pepsin, and digestive enzymes as found in the stomach and upper small intestine, and therefore will not release their contents while transiting the stomach or upper small intestine.

In all embodiments of the invention, most of the deer velvet powder contained in a DRcaps™ delayed release capsule are released in the lower small intestine for maximized micellar absorption in the terminal ilium. These micelles carry the delicate molecules of the pristine deer velvet via gut circulation and liver splanchnic circulation to the general circulation to all organs of the body for promoting regeneration.

At least half of the deer velvet contained in a DRcaps™ capsule is released in the terminal ileum, and more often the vast majority of the deer velvet powder contained in a DRcaps™ capsule is released at the ideal location along the lower small intestine, i.e., within the terminal ilium for unaltered molecular delivery of at least 300 biomolecules and at least six growth hormones to the body.

The deer velvet does is not beneficially absorbed in other parts of gastrointestinal tract, either before or after the terminal ilium of the small intestine. Thus, the deer velvet powder must be delivered to the end of the small intestine. Delivery of the deer velvet powder to regions in the small intestine above the terminal ilium region, or further down into the cecum of the large intestine, are much less efficacious.

The ileum is the third and end portion of the small intestine. It follows the jejunum and terminates at the ileocecal junction, where the terminal ileum communicates with the cecum of the large intestine through the ileocecal valve.

Residual digestive enzymes in the jejunum will destroy much of the molecular structure of the hormones, and building block and transducer molecules, thereby reducing the value of the deer velvet powder to the body.

The deer velvet powder has much less value when absorbed AFTER the terminal ileum, such as in the cecum. The deer velvet powder must be primarily delivered to the only major absorption region, i.e., to the ileum.

There are other brands of deer velvet powder other than Mountain Red™ Deer Velvet powder, which are also high quality, anesthetic free forms, with proper maximized harvesting with peak molecular timing for collection coordinated with the date and season for best molecular and hormonal content.

For example, Waitipi is another company in New Zealand that uses identical pneumatic bladder capture of animals in dark huts for careful antler recovery and gentle animal recovery without anesthetic. The deer velvet is then independently carefully ground off the antlers without including antler bone for the harvest and encapsulation.

DRcaps® are tested to survive prolonged exposure to pH 2.0 in the stomach, allowing most of the caps to transit the stomach so as to open only upon reaching the small intestine, and then release the deer velvet in the capsule along the lower small intestine such that all of the deer velvet can be absorbed as it transits through the terminal ilium at the end of the small intestine.

The delayed release capsule includes hypromellose (HPMC), and a gelling agent. Deer velvet is released about 50 minutes after swallowing the delayed release capsule.

To ensure low moisture before encapsulation, the deer velvet powder to be encapsulated should be shipped overnight in a manner so as to maintain sterile conditions, and should be refrigerated before encapsulation so as to maintain low moisture before encapsulation.

DRCaps® delayed release capsules are very acid resistant, whereas standard gelatin capsules are broken down in the acid environment of the stomach. Thus, DRcaps® delayed release capsules allow most of the contents to ride unaltered through the stomach and through most of the small intestine to be released, and then micellized, in the terminal ileum. The micellized deer velvet then enters the splanchnic circulation, and then the central circulation to be carried by the circulatory system to facilitate organ regeneration.

Other modifications and implementations will occur to those skilled in the art without departing from the spirit and the scope of the invention as claimed. Accordingly, the above description is not intended to limit the invention, except as indicated in the following claims.

What is claimed is:

1. A capsule of deer velvet powder for ensuring delivery of unaltered molecules of the deer velvet powder systemically to organs of a body, the body having a stomach and a small intestine, the small intestine having a terminal ileum, the capsule of deer velvet powder comprising:
    a delayed release capsule; and
    a quantity of deer velvet powder contained within the delayed release capsule,
    the delayed release capsule made using hydroxypropyl methylcellulose, and
    the delayed release capsule configured to resist digestive processes in the stomach so as to release the quantity of deer velvet powder substantially along the small intestine, thereby ensuring micellization and absorption of various components of the deer velvet powder along the terminal ileum.

2. The capsule of claim 1, wherein the delayed release capsule is of size 00.

3. The capsule of claim 1, wherein the quantity of deer velvet powder is substantially 500 mg.

4. The capsule of claim 1, wherein the delayed release capsule is configured to release the quantity of deer velvet powder substantially 50 minutes after swallowing the delayed release capsule.

5. The capsule of claim 1, wherein the delayed release capsule includes a gelling agent.

6. The capsule of claim 1, wherein the quantity of deer velvet powder is anesthetic-free.

7. The capsule of claim 1, wherein the quantity of deer velvet powder is obtained by grinding the deer velvet powder off antlers of a deer without including antler bone.

8. The capsule of claim 1, wherein the quantity of deer velvet powder is obtained by using pneumatic bladder capture of animals in dark huts for antler recovery and gentle animal recovery without anesthetic.

9. A method for manufacturing a capsule of deer velvet powder for ensuring delivery of unaltered molecules of the deer velvet powder systemically to organs of a body, the body having a stomach and a small intestine, the small intestine having a terminal ileum, the method comprising:
    obtaining an unfilled delayed release capsule which is:
        (i) made using hydroxypropyl methylcellulose;
        (ii) configured to contain a quantity of deer velvet powder; and
        (iii) configured to resist digestive processes in the stomach so as to release the deer velvet powder substantially along the small intestine, thereby ensuring micellization and absorption of various components of the deer velvet powder along the terminal ileum;
    obtaining a quantity of deer velvet powder; and
    filling the unfilled delayed release capsule with the quantity of deer velvet powder to provide the capsule of deer velvet powder.

10. The method for manufacturing of claim 9, wherein the unfilled delayed release capsule is of size 00.

11. The method for manufacturing of claim 9, wherein the quantity of deer velvet powder is substantially 500 mg.

12. The method for manufacturing of claim 9, wherein the unfilled delayed release capsule is configured to release the quantity of deer velvet powder during transit through the small intestine about 50 minutes after swallowing the capsule of deer velvet powder.

13. A method for naturally promoting micellization of deer velvet powder so as to deliver unaltered molecules of the deer velvet powder systemically to organs of a body, the body having a stomach and a small intestine, the small intestine having a terminal ileum, the method comprising:
    swallowing a delayed release capsule containing a quantity of deer velvet powder,
    the delayed release capsule having been made using hydroxypropyl methylcellulose, and
    the delayed release capsule configured to resist digestive processes in the stomach so as to release the deer velvet powder substantially along the small intestine, thereby ensuring micellization of various components of the deer velvet powder along the terminal ileum.

14. The method of claim 13, wherein the delayed release capsule is acid resistant, so as to transit the stomach and enter the lower small intestine before releasing the deer velvet powder.

* * * * *